US009040488B2

(12) United States Patent
Block et al.

(10) Patent No.: US 9,040,488 B2
(45) Date of Patent: May 26, 2015

(54) IMINO SUGAR DERIVATIVES DEMONSTRATE POTENT ANTIVIRAL ACTIVITY AND REDUCED TOXICITY

(75) Inventors: Timothy M. Block, Doylestown, PA (US); Jinhong Chang, Chalfont, PA (US); Xiaodong Xu, Doylestown, PA (US)

(73) Assignees: Baruch S. Blumberg Institute, Doylestown, PA (US); Drexel University, Philadelphia, PA (US)

( * ) Notice: Subject to any disclaimer, the term of this patent is extended or adjusted under 35 U.S.C. 154(b) by 300 days.

(21) Appl. No.: 13/061,734

(22) PCT Filed: Sep. 2, 2009

(86) PCT No.: PCT/US2009/055658
§ 371 (c)(1),
(2), (4) Date: Mar. 2, 2011

(87) PCT Pub. No.: WO2010/027996
PCT Pub. Date: Mar. 11, 2010

(65) Prior Publication Data
US 2011/0189771 A1 Aug. 4, 2011

Related U.S. Application Data

(60) Provisional application No. 61/190,618, filed on Sep. 2, 2008.

(51) Int. Cl.
C07D 211/46 (2006.01)
A61K 31/445 (2006.01)
(Continued)

(52) U.S. Cl.
CPC .............. *A61K 31/47* (2013.01); *C07D 211/46* (2013.01); *A61K 31/7056* (2013.01)

(58) Field of Classification Search
None
See application file for complete search history.

(56) References Cited

U.S. PATENT DOCUMENTS 4,407,809 A * 10/1983 Junge et al. .................... 514/319
5,051,407 A * 9/1991 Boshagen et al. .............. 514/24
6,545,021 B1 * 4/2003 Mueller et al. ................. 514/318

OTHER PUBLICATIONS

Vippagunta et al., "Crystalline Solids" Advanved Drug Delivery Reviews (2001) vol. 48 pp. 3-26.*

(Continued)

*Primary Examiner* — Eric Olson
(74) *Attorney, Agent, or Firm* — Joseph F. Aceto

(57) ABSTRACT

Imino sugars, such as deoxynojirimycin (DNJ), are glucose analogues that selectively inhibit cellular α-glucosidase I and II (enzymes that process N-linked glycans in glycoprotein) and exhibit broad spectrum antiviral activities against many enveloped viruses. Previously we have reported a novel DNJ derivative, OSL-95II, with antiviral activity and reduced cytotoxicity. In order to develop imino sugars with more potent antiviral activity as well as improved toxicity profile, OSL-95II was modified by diversifying the nitrogen linked alkylated side chain. The antiviral activities were initially tested in bovine viral diarrhea virus (BVDV) infected MDBK cells, yielding several imino sugar derivatives with novel structure and superior antiviral activity and toxicity profile. Furthermore, these new compounds were shown to be active against Dengue virus (DV) and West Nile virus (WNV) infection in BHK cells where potent anti-DV activity having submicromolar EC50 values and SI of greater than 900. These compounds represent a new generation of iminio sugars and their analogues, having application in the clinical treatment of infection of DV and other members of flaviviridae.

6 Claims, 8 Drawing Sheets

Figure 1:
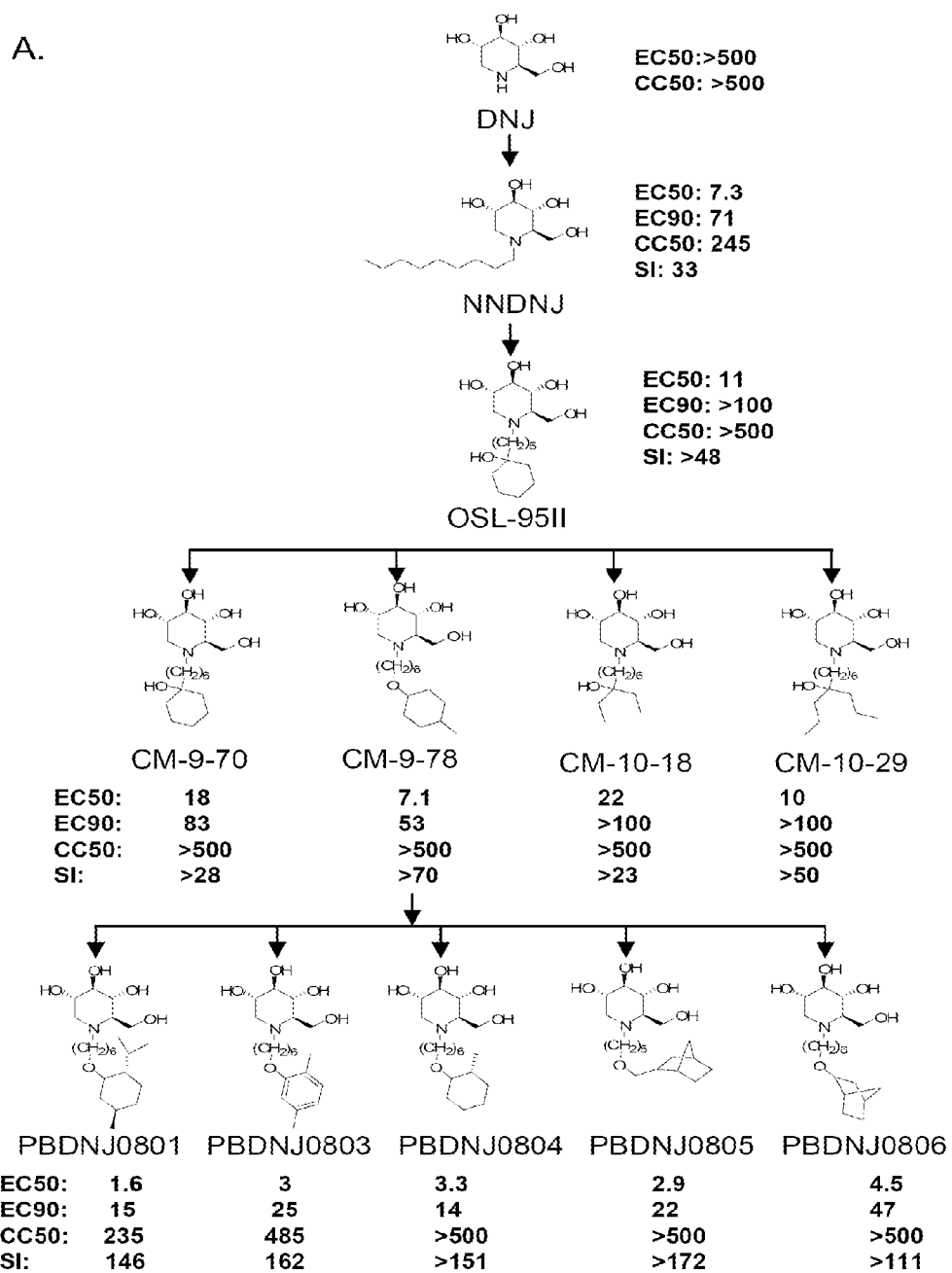
Figure 1:
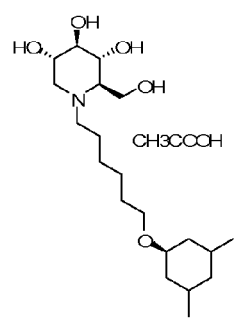
Figure 1:
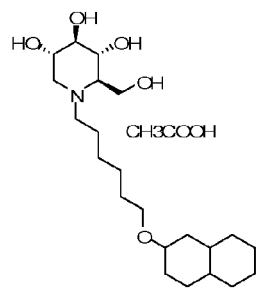
Figure 1:
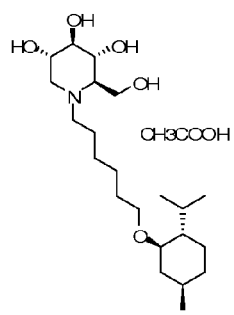
Figure 1:
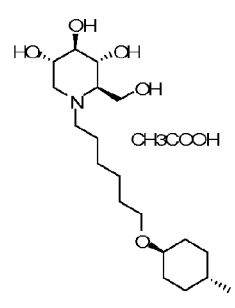
Figure 1:
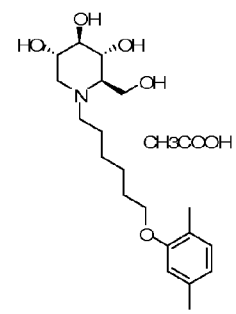
Figure 1:
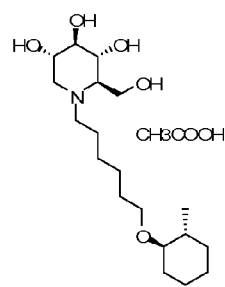
Figure 1:
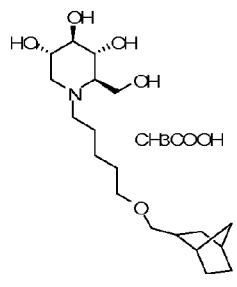
Figure 1:
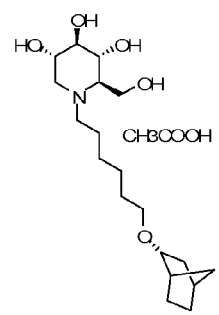

A.

B.

(51) Int. Cl.
*A61K 31/47* (2006.01)
*A61K 31/7056* (2006.01)

(56) References Cited

OTHER PUBLICATIONS

Jain et al., "Polymorphism in Pharmacy" Indian Drugs (1986) vol. 23 No. 6 pp. 315-329.*
Braga et al., "Making Crystals from Crystals: a green route to crystal engineering and polymorphism" Chemcomm (2005) pp. 3635-3645.*
Lieberman et al., "Pharmaceutical Dosage Forms: Tablets" published 1990 by Marcel Dekker, Inc, pp. 462-472.*
FDA product label for Copegus® (Ribavirin) pp. 1-34, initial approval in 2002, downloaded from www.accessdata.fda.gov.*
Barthet al., "Cellular Binding of Hepatitis C Virus Envelope Glycoprotein E2 Requires Cell Surface Heparan Sulfate" The Journal of Biological Chemistry (2003) vol. 278 No. 42 pp. 41003-41012.*

* cited by examiner

B.

PBDNJ-0807-A

PBDNJ-0808-A

PBDNJ-0801-A

PBDNJ-0802-A

PBDNJ-0803-A

PBDNJ-0804-A

PBDNJ-0805-A

PBDNJ-0806-A

A.

B.

IMINO SUGAR DERIVATIVES DEMONSTRATE POTENT ANTIVIRAL ACTIVITY AND REDUCED TOXICITY

CROSS REFERENCE TO RELATED APPLICATIONS

This application is a non-provisional application, the entire contents of which is incorporated by reference herein and claims priority, in part, of U.S. Provisional Application No. 61/190,618, filed 2 Sep. 2008 and International Application PCT/US2009/055658, filed 2 Sep. 2009.

BACKGROUND

1. Field

This invention relates to the field of antiviral compounds and compositions for the treatment against flaviviral infections. More specifically, it relates to N-pentyl-(1-hydroxycyclohexyl)-DNJ derivatives and their use as pharmaceutical compositions in the treatment and prevention of Dengue, West Nile, Japanese Encephalitis virus, Bovine viral diarrhea virus, and hepatitis C.

2. Background Art

Imino sugars are broad-spectrum antiviral agents that interfere with virus assembly through glucosidase inhibition. Dengue virus has an envelope protein with a specific structure that makes it more sensitive to imino sugar treatment. Consistent with this notion is the observation that virion production of many types of enveloped viruses, including hepatitis B virus, human immunodeficiency virus, herpes simplex virus-1, influenza viruses, parainfluenza virus, measles virus as well as several members of flaviviridae family, such as bovine viral diarrhea virus (BVDV), dengue virus (DV), West Nile virus (WNV), Japanese encephalitis virus (JEV) and hepatitis C virus, can be inhibited by α-glucosidases inhibitors, such as deoxynojirimycin (DNJ) and its derivatives.

As a substrate analog, some imino sugar derivatives can competitively inhibit the activity of α-glucosidases I and II in endoplasmic reticulum (ER). ER α-glucosidases are enzymes that catalyze the first step trimming of glucose from the high-mannose N-linked glycan structure attached to the nascent glycoproteins. Proper processing of the terminal glucose residues from N-linked glycans is critical for the subsequent interaction between glycoprotein and ER chaperones calnexin and calreticulin. For some, but not all of the glycoproteins, this interaction is required for the correct folding and sorting. Thus, inhibition of α-glucosidases leads to the misfolding and degradation of glycoproteins where this specific interaction is required.

Viral envelope proteins are usually glycoproteins. It has been shown that for many types of enveloped viruses, such as hepatitis B virus, human immunodeficiency virus, herpes simplex virus 1 as well as several members of flaviviridae family, their viral envelope glycoproteins depend on the calnexin/calreticulin mediated folding pathway. Thus alteration of glycan structure on envelope protein by an α-glucosidase inhibitor such as imino sugars interfere with the maturation of viral envelope proteins, and as a consequence, viral particle assembly and/or secretion can be inhibited. In some cases, viral particles carrying altered glycan structure also demonstrated reduced infectivity. Therefore, glucosidase inhibitors are applicable as broad spectrum antivirals against many types of enveloped viruses.

Folding and maturation of envelope proteins of flaviviruses are extremely sensitive to glucosidase inhibition. Antiviral activity of imino sugars has been shown for both in vitro and in vivo experiments, against Dengue virus (DV), West Nile virus (WNV) and Japanese encephalitis virus (JEV). Recently, another member of flaviviridae, hepatitis C virus (HCV), was shown to be sensitive to imino sugar treatment in tissue culture. In many studies, Bovine Viral Diarrhea Virus (BVDV), which belongs to pestivirus of flaviviridae has been used as model system for flavivirus such as DV and WNV, as well as HCV.

The development of a imino sugar glucosidase inhibitor is limited by low efficacy and/or cytotoxicity. The prototype imino sugar, deoxynojirimycin (DNJ), requires millimolar concentrations to achieve 50% inhibition in virus yield reduction assays (EC50). Modification of DNJ by adding alkylated side chains on the nitrogen atom, improved antiviral efficacy. For example, N-nonyl-DNJ (NNDNJ), which is a DNJ derivative with a nine-carbon alkyl side chain, reduced EC50 to a lower micromolar level. However, NNDNJ also showed higher cytotoxicity. Hence, the present invention describes a chemical modification on the nitrogen linked alkylated side, chain to improve both efficacy and cytotoxicity profiles.

Generally, hemorrhagic fever viruses (HFV) are a group of diseases, caused by enveloped, single-stranded RNA viruses from four different virus families, that are acquired through contact with animals or the bite of an infected arthropod. Table 1 summarizes viruses from these four families that are included in NIAID category A of potential bioterror agents.

TABLE 1

Summary of NIAID category A agents that cause VHF

| Family | Genome | virus | Fatality | Virions | Clinical feature/Pathogenesis |
|---|---|---|---|---|---|
| Filoviridae | Non-segmented Negative-sense | Ebola virus (Zaire) Marburg | 60-90% 23-70% | Enveloped with glycosylated | Disseminated intravascular coagulation (DIC) |
| Arenaviride | Bi-segmented Negative-sense (Ambisense) | Junin virus/Machupo virus | 15-30% | viral Glycoprotein(s) | Bleeding/Thombocytopenia Lymphocyte Apoptosis/Depletion |
| Bunyaviridae | Tri-segmented Negative-sense (Ambisense) | Hantavirus Rift Valley Fever virus | 5-15% 1% | | Macrophage infection Dendritic Cell infection Cytokine tsunami |
| Flaviviridae | Non-segmented Positive-sense | Dengue virus | 1-5% | | |

More specifically, Dengue virus (DV) infection is a growing world health problem and a bio-terror concern. DV is mosquito-borne flavivirus that causes lethal hemorrhagic fever in people. The global burden of dengue has grown dramatically in recent decades, and it is currently classified as a re-emerging infectious diseases. Dengue fever (DF) and dengue haemorrhagic fever (DHF)/dengue shock syndrome (DSS) occur in over 100 countries, with more than 2.5 billion people at risk and an estimated 50 million infections each year with 500,000 hospitalized cases and 25,000 deaths. Although the major disease burden is mainly found in the tropical/sub-tropical regions of south-east Asia and the western Pacific, with globalization of the world accompanied by gradual shift in global climate, there are increased reports of dengue related diseases in America and other developed countries. Moreover, due to the feature of dengue virus to grow in high titer in cell culture and the infectability in aerosol form, it has been identified as one of the priority concern for bio-terror control.

Thus far, effective antiviral therapies and vaccines are not yet available to treat or prevent DV infection. For the control of DV infection, in addition to better insecticides, rapid diagnostics, safe vaccine, it seems likely that strategic use of antivirals, during periods of viremia, would be beneficial. DHF and DSS are considered to directly correlate with higher titer of viremia, therefore, antivirals that can lower viral load by 2 logs or greater are anticipated to reduce serious dengue diseases, decrease mortality associated with pandemic and slow down transmission.

Chemotherapy against dengue virus infection can be developed by two principally different approaches, blocking the virus coded functions or the cellular functions needed for virus replication. Although targeting host functions has the potential to hamper normal cellular activity, it is advantageous in the way that the therapy may be active against many viruses using similar pathway. Moreover, the emergence of resistant virus would be expected to be rare. Recently, antivirals targeting the host factors become more attractive, since some treatments, such as the one we proposed using imino sugar targeting host glucosidase, demonstrated high selectivity against virus over cellular function, especially for short period of treatment during acute virus infection such as dengue infection.

Previously the imino sugar derivative N-pentyl-(1-hydroxycyclohexyl)-DNJ (OSL-95II) has been identified as having micromolar antiviral activity (US 2009/0042268, incorporated by reference in its entirety). Compared to NNDNJ, OSL-95II has reduced cytotoxicity but retains micromolar antiviral activity against BVDV, DV and WNV infection. The characteristic feature of OSL-95II is a 5-carbon alkylated side chain with a terminal ring structure. In the present invention, OSL-95II is modified by changing the length and/or composition of nitrogen linked side chain, resulting in a new structural type of imino sugars with not only better toxicity profile, but also superior antiviral activity against BVDV, DV and WNV infection. For DV infection, the present invention provides imino sugar derivatives having EC90 values in submicromolar concentration indicating their potential to be candidate for further clinical development as therapeutic agents.

SUMMARY OF THE INVENTION

The present invention provides a new class of compounds with antiviral activity and reduced cytotoxicity against BVDV, DV and WNV. These compounds are developed through an optimization of the nitrogen-linked alkylated side chain structure, having activity against enveloped virus.

29 structurally-related compounds having alkylated DNJs with cyclized side chains of OSL-95II were synthesized and evaluated, among which, a group of compounds, as represented by CM-9-78, with oxygenated alkyl chain and terminal ring structure stood out to have better efficacy and lower cytotoxicity. Further modification of terminal ring structure on CM-9-78 resulted in the PBDNJ series of compounds, which have a high potency for inhibition of DV infection in vitro with EC90 values at submicromolar concentrations. This group of PBDNJ compounds are representative of a class of compounds whereby realistic candidates for the development of antiviral therapy against human dengue virus infections and other clinically relevant disorders are possible.

DESCRIPTION OF THE FIGURES

FIG. 1: Panel A, Chart representing the structure and the activity against BVDV. Panel B Structural representation of 8 analogs from the PBDNJ group of compounds.

FIG. 2: Dose dependent inhibition of Junin virus infection by iminio sugar derivatives. Vero cells were infected with Junin virus at an MOI of 0.1 followed by treatment with compounds. Supernatants were harvested after 48 hours and subjected to plaque assay.

FIG. 3: Combination effects of imino sugar and ribavirin in dengue infected cells.

FIG. 4: Combination effects of imino sugar and ribavirin in dengue infected mice.

FIG. 5: Imino sugar treatment of cells infected with HCV. Treatment was performed with 100 uM concentration of compounds. HCV virus titer was assayed using TCID50 yield reduction assay.

FIG. 6: Modification on nitrogen-linked alkylated side chain on OSL-95II. Panel A. Structures of prototype alkylated DNJ, NNDNJ, our previous lead alkylated NDJ derivative OSL-95II. Modifications were made based on OSL-95II which change the length of the alkylated chain (CM-9-70), substitute the terminal ring structure (CM-10-29 and CM-10-18) and move of oxygen atom to the alkylated chain (CM-9-78). Panel B. Anti-BVDV activity of the compounds. MDBK cells were infected with BVDV (1 m.o.i.) for 1 hour. After removal of virus, compounds were added at indicated concentrations. Supernatants were harvested 24 hour post infection for plaque assay to determine the reduction on virus titers.

FIG. 7: Chemical structure and antiviral effect of CM-9-78 derivatives. Panel A. Structures of CM-9-78 and its derivatives with modification on the terminal ring. Panel B. Antiviral activity of CM-9-78 and its derivatives. BVDV infection was as in FIG. 1. Cells were treated with compounds with indicated concentration. Virus titers in the supernatant were assayed as described for FIG. 1.

DETAILED DESCRIPTION

Despite great potential, clinical development of imino sugars has been limited by their relatively low efficacy and unfavorable toxicity profiles. N-butyl-DNJ (NBDNJ, currently approved by the US and European FDAs for use in the management of Gaucher's disease) and Cellgosovir (in Phase II trials for HCV) both require near millimolar concentrations to achieve $IC_{50}$ values, in tissue culture, against their target viruses. These concentrations are difficult to achieve in vivo, and thus their antiviral utility is limited. For example, NBDNJ was evaluated in Phase II clinical trials as an anti-HIV agent, but it was not possible to achieve sufficiently high serum concentrations for the drug, and no major impact was observed on viraemia.

A great deal has been learned from mechanistic as well as medicinal chemistry study of the imino sugars. Considerable effort has been focused on the medicinal chemistry modification of imino sugar to improve the efficacy and toxicity profiles (Block and Jordan, 2001; Block et al., 1998; Block et al., 1994; Dwek et al., 2002; Gu et al., 2007; Jordan et al., 2002; Kuriyama et al., 2008; Mehta et al., 2001; Mehta et al., 2002; Minami et al., 2008; Zitzmann et al., 1999). From a structural perspective, alkylated imino sugars contain two distinct molecular elements, the imino sugar head group DNJ and nitrogen-linked alkyl side chain. While the DNJ head confers competitive α-glucosidase inhibition, the nitrogen-linked side chain determines potency and cytotoxicity, and the latter provides major points of chemical modification (Block and Jordan, 2001; Gu et al., 2007; Mehta et al., 2002). Compared with DNJ or DNJ derivatives with short alkyl side chains such as NBDNJ, which has an EC50 of at least 100-500 mM in tissue culture against test viruses such as BVDV and DV, DNJs with longer alkyl side chains, such as N-nonyl-DNJ (NNDNJ), are 100 times more potent and thus were considered to be significant improvements from DNJ and NBDNJ. However, NNDNJ was shown to be more cytotoxic than NBDNJ or DNJ.

In an effort to optimize the nitrogen linked alkylated side chain structure, N-pentyl-(1-hydroxycyclohexyl)-DNJ (OSL-95II) was produced, which has reduced cytotoxicity while retaining micromolar antiviral activity against BVDV, DV and WNV. 29 structurally-related compounds were synthesized and evaluated, among which, a group of compounds, as represented by CM-9-78, with oxygenated alkyl chain and terminal ring structure stood out to have better efficacy and lower cytotoxicity. Further modification of terminal ring structure on CM-9-78 resulted in a series of compounds with high potency in the inhibition of DV infection in vitro having EC90 values at submicromolar concentrations. These compounds represent a class of compounds that may provide candidates for the development of antiviral therapy against such infections as human dengue virus infections (FIG. 1 Panel A).

The compounds are synthesized with alkoxycycloalkyl and alkoxyaromatic side chains through the reaction of DNJ with corresponding aldehydes under hydrogenation conditions in the presence of Pd/C. Alternatively, these reactions can be carried out using typical reductive amination conditions employing sodium cyanoborohydride as a reducing agent. The final compounds are purified by column chromatography and/or re-crystallization. Several selected analogs, while not meant to be limiting, are shown in FIG. 1, Panel B.

To improve antiviral activity of CM-9-78, the influence of constituent and/or aromatization of the terminal ring structure on antiviral efficacy and cytotoxicity were further developed (FIG. 1). PBDNJ0801 and PBDNJ0804 represent compounds with alkyl substitution on the cyclohexyl ring. In PBDNJ0803, the cyclohexyl ring was replaced with the 2,5-dimethylphenyl aromatic group. PBDNJ0805 and PBDNJ0806 differ in the position of the oxygen atom at the alkyl side chain while employing a conformational restriction strategy with a bridged cyclohexyl group at the terminal ring. All of these PBNDJ compounds were more potent than NNDNJ, OSL-95II and CM-9-78. In addition most of them show lower toxicity than NNDNJ, leading to significantly improved SI.

Figure 2:
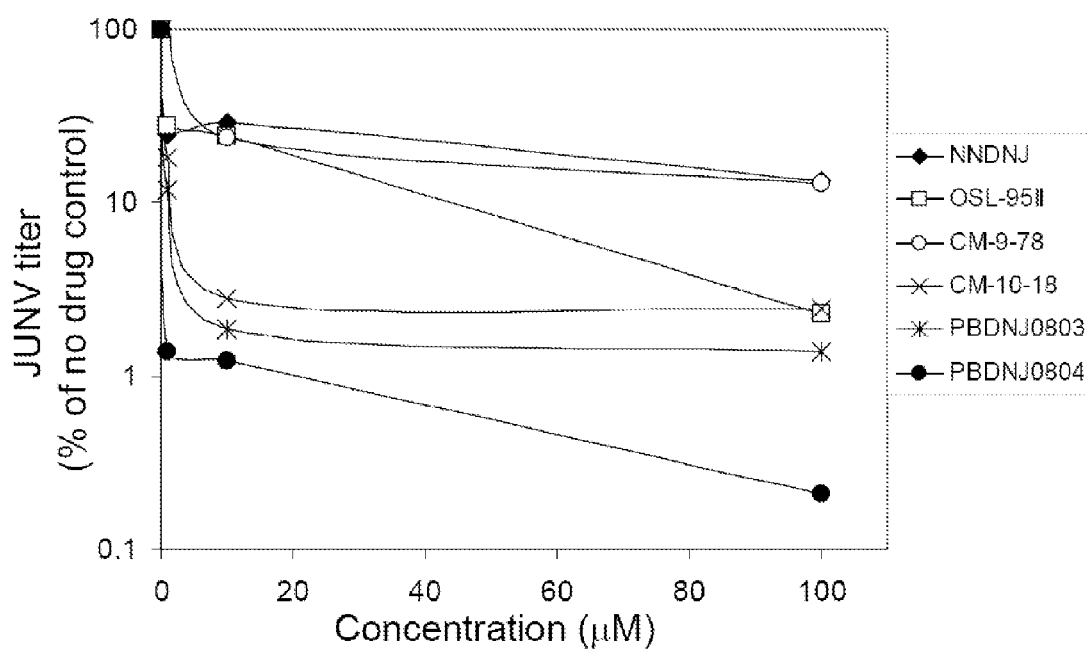

To directly test the antiviral effects of the novel imino sugar derivatives against medically important human pathogenic flaviviruses as well as hemorrhagic arenaviruses, the antiviral effect of CM-9-78 and PBDNJ compounds on Dengue (serotype II, New Guinea C strain), West Nile (2002 Texas isolate), Ebola (Zaire strain), Tacaribe virus (21573 strain) and Junin virus (JUNV, Romero strain) were examined. As represented in FIG. 2, using non-toxic concentrations, all the compounds demonstrated dose dependent antiviral activity against Junin virus infection, with PBDNJ0803 and 0804 being the most potent.

Consistent with this observation, the extraordinary activity of PBDNJ compounds was also shown in cells infected with Dengue, West Nile viruses as well as Ebola and Tacaribe viruses. As summarized in Table 2, similar to the result obtained from Junin virus testing, PBDNJ0804 is also the most potent compound against Ebola and Dengue viruses, with $EC_{50}$ at submicromolar levels and $EC_{90}$ values of sub- or low micromolar levels, and the SI's were all greater than 800. These results support the broad-spectrum antiviral nature of imino sugar glucosidase inhibitors and the value of using surrogate viruses for screening.

TABLE 2

Imino sugar compounds and their varying antiviral activities (in micromolar)

| | Dengue | | West Nile | | | Ebola | | Tacaribe | | Junin | | |
| --- | --- | --- | --- | --- | --- | --- | --- | --- | --- | --- | --- | --- |
| | $EC_{50}$ | $EC_{90}$ | $EC_{50}$ | $EC_{90}$ | * $CC_{50}$ | $EC_{50}$ | $EC_{90}$ | $EC_{50}$ | $EC_{90}$ | $EC_{50}$ | $EC_{90}$ | # $CC_{50}$ |
| DNJ | –500 | ND | >500 | ND | 20-100 | ND | ND | ND | ND | ND | ND | ND |
| NBDNJ | –100 | ND | >100 | ND | 20-100 | ND | ND | ND | ND | ND | ND | ND |
| NNDNJ | 1-4 | 3-10 | 4 | ND | 20-100 | 12 | 85 | 3 | 70 | 0.7 | >100 | 100 |
| OSL95-II | 4 | 8.7 | 4.5 | ND | >100 | 0.6 | 8 | 29 | >100 | 0.75 | 68 | >500 |
| CM-9-78 | 6.8 | 13 | ND | ND | >100 | 7.5 | >100 | 10 | >100 | 2 | >100 | >500 |
| PBDNJ0801 | 0.1 | 0.2 | 4.75 | 19 | 80 | ND | ND | ND | ND | ND | ND | ND |
| PBDNJ0803 | 0.1 | 0.6 | 1.5 | 20 | 85 | ND | ND | 2 | 75 | 0.5 | 2 | 300 |
| PBDNJ0804 | 0.08 | 0.6 | 3.5 | 33 | 65 | 0.5 | 5 | 1.5 | 50 | 0.45 | 0.9 | 500 |

EC50 and EC90 determined by yield reduction assay
* determined in BHK cells (for Dengue and West Nile virus) with 3 days treatment
assayed in vero cells (for Ebola, Tacaribe and Junin virus) with 3 days treatment Thus, the present invention describes chemical modifications of imino sugars for a group of structurally related compounds with broad-spectrum and highly potent antiviral activity against hemorrhagic fever viruses.

Pharmacokinetic (PK) profiles of oral and intraperitoneal (IP) injections of one of the lead compounds, CM-9-78 suggests that oral administration resulted in higher peak serum compound concentrations and longer half life (data not shown). Single dose oral administration of CM-9-78, at 100 mg/Kg, resulted in a plasma concentration above 30 μM for at least 10 hours. This suggests that oral administration of even more potent imino sugar antivirals, such as PBDNJ with sub- or low micromolar $EC_{90}$ values, is likely to offer realistic candidates for the development of antiviral therapeutics against human virus infection causing VHFs. In addition, intraperitoneal and oral administration of up to 100 mg/kg of CM-9-78 were both well tolerated as judged by the body weight and food consumption.

Figure 3:
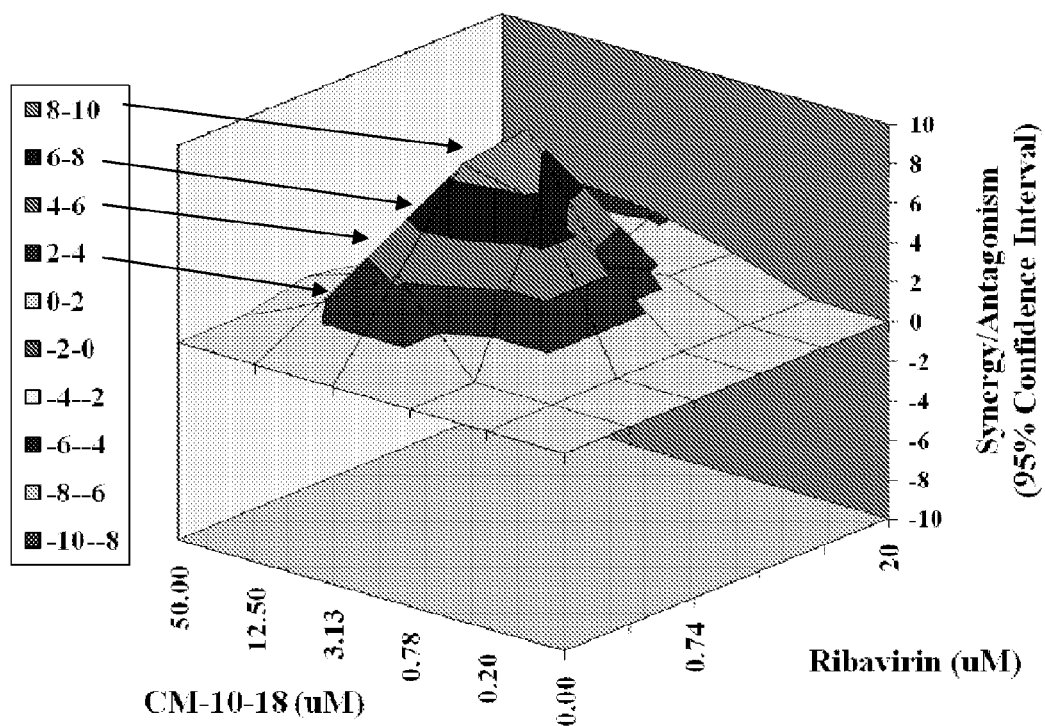
Figure 4:
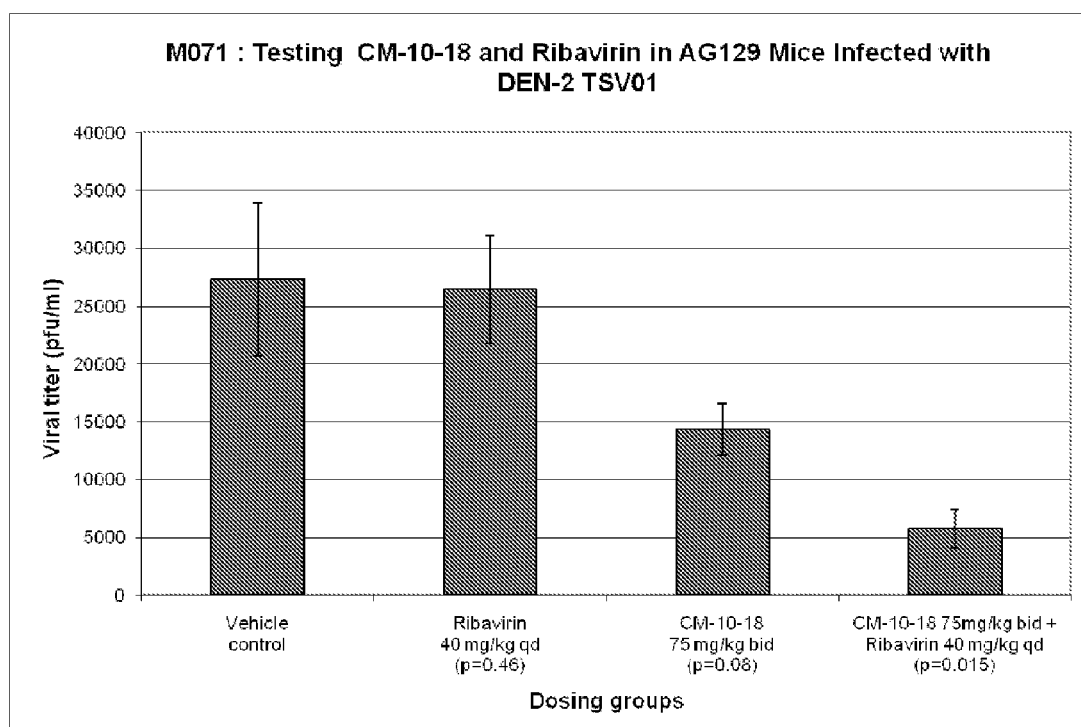

Another embodiment of the present invention is the use of imino sugars in combination with ribavirin to provide synergistic antiviral effects against dengue infection. Ribavirin, a putative IMP dehydrogenase inhibitor, is an FDA approved drug with broad-spectrum antiviral activity against many types of viruses including Arenavirus, Bunyavirus. However, the clinical use of ribavirin has been significantly limited by dose-limiting toxicity leading to severe anemia. Nevertheless, it has been used with limited success in the treatment of viral hepatitis C, when used in combination with interferon. The present invention considers the use of CM-10-18 and ribavirin for synergistic antiviral effects against dengue infection. Support for this is shown in both cell culture (FIG. 3) and infected mice (FIG. 4).

Given their likely distinct mechanisms, it is not surprising that these two compounds exert combination antiviral effects that appear to be better than would be expected if they were just added in dose. Combinations with other compounds with antiviral effects such as, but not limited to, ribavirin, can provide significant therapeutic value for clinical VHF diseases.

Figure 5:
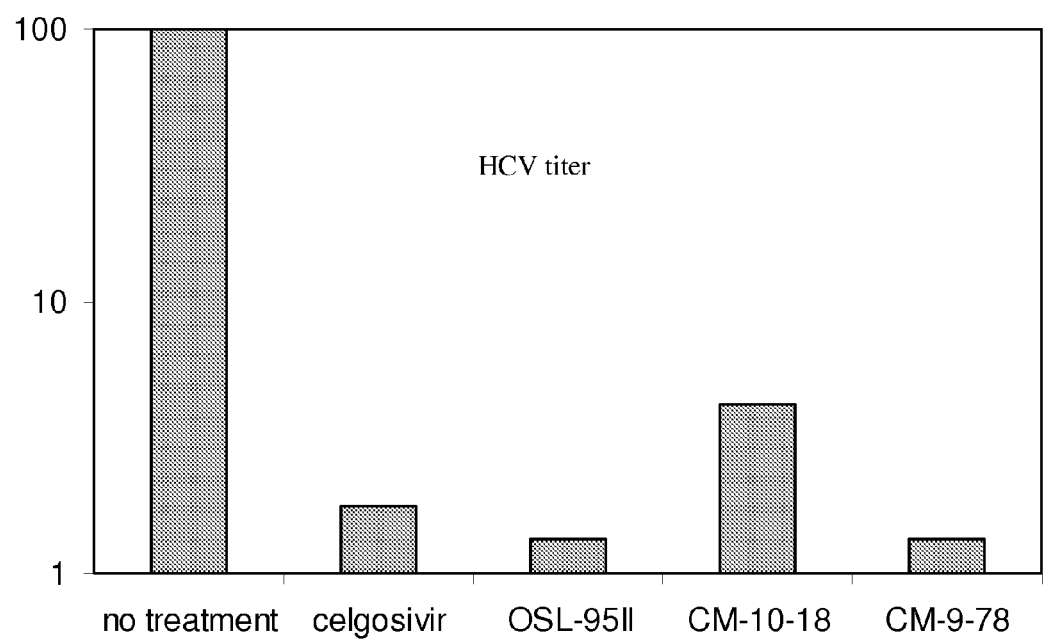

Another embodiment of the present invention is the use of imino sugar glucosidase inhibitors in the treatment of HCV. Imino sugar glucosidase inhibitors show equal or better efficacy than celgosivir. Table 3 shows that the imino sugar derivatives demonstrated better EC50 and/or EC90 against NNDNJ and Castanospermin, and similar antiviral efficacy than celgosivir, as measured by intracellular HCV RNA level using real-time RT-PCR. FIG. 5 shows that using a 100 μM nontoxic dose, these imino sugars demonstrated equal or better efficacy than celgosivir.

TABLE 3

Imino sugar derivatives against HCV infection

|  | $EC_{50}$ | $EC_{90}$ | $CC_{50}$ |
| --- | --- | --- | --- |
| NNDNJ | 2.5 | >500 | 280 |
| Castano. | 295 | >500 | >500 |
| Celgosivir | 3.8 | 100 | >500 |
| OSL-95II | 6 | 125 | >500 |
| CM-10-18 | 2 | 55 | >500 |
| CM-9-78 | 5 | 160 | >500 |

EXAMPLE 1

Introduction of Oxygenated and Terminal Ring Structures into the Nitrogen-Linked Alkylated Side Chain of Deoxynojirimycin Materials and Methods Cells and viruses. BVDV-free MDBK cells (CCL 22) were obtained from the American Type Culture Collection and propagated in DMEM/F12 essential medium supplemented with penicillin (500 U/ml), streptomycin (500 U/ml), and 10% heat inactivated horse serum (Invitrogen). Cells were maintained in a humidified incubator at 37° C. with 5% CO2. BVDV (NADL strain). For infections, virus inoculum was added in complete medium and adsorbed for 1 hour at 37° C., the inoculum was then removed, the cells washed once with medium and fresh medium containing compounds added. Virus stocks were prepared by freeze-thawing the infected cells and culture supernatant three times followed by centrifugation at 1,000 g for 5 min. Stock titers were determined, and stocks were aliquoted and stored at −80° C. WNV was obtained from a cDNA clone of a human 2002 isolate from Texas; virus obtained from BHK cells electroporated with the in vitro synthesized RNA from this cDNA clone was passaged in Vero cells before use in antiviral assays. Dengue virus (DV) serotype 2 was a New Guinea C virus that had been passaged 28 times in suckling mouse brain, twice in Vero cells, and once in C6/36 mosquito cells.

BVDV antiviral and plaque assays. To evaluate antiviral activity against BVDV, a single cycle virus yield reduction assay was performed in the presence of various concentrations of the test compounds. Specifically, $2 \times 10^5$ MDBK cells/well were plated in 24 well plates. Twenty-four hours later, the cells were infected with BVDV at a multiplicity of infection (moi) of 0.5 PFU/cell in 100 ul complete media. After adsorption for 1 h at 37° C., the inoculum was removed, and cells were washed with media before media containing vehicle or various concentrations of each compound was added. At 22 hour post infection, both cell and media were collected and freeze-thawed three times before the virus was titered. For BVDV virus titer determination, $10^{-2}$, $10^{-3}$, and $10^{-4}$ dilutions of virus were inoculated onto MDBK cells as described previously. After absorption and washing the cells were overlaid with medium containing methylcellulose or soft agar and incubated at 37° C. for 3 days or until plaques were visible. Plaques were counted directly under the microscope or after staining with crystal violet in 70% methanol for 15 min.

WNV and DV Yield Reduction assay: Antiviral activity against WNV was evaluated in a yield reduction assay. Briefly, BHK cells were plated in 96-well plates at a concentration of $2.5 \times 10^4$ cells/well. 24 hours after plating, the cells were infected with WNV at an MOI of 0.05. After 1 hour the inoculum was aspirated and the cells re-fed with fresh DMEM containing dilutions of the test compounds. Plates were then incubated at 37° C. for 48 hours, the supernatant collected and the WNV produced titered. For virus titration, Vero cells were plated in 96-well plates at $8.0 \times 10^3$ cells/well and incubated overnight. The Vero cell monolayers were then infected for 1 hour with various dilutions of the WNV supernatant, overlaid with media containing 0.6% tragacanth (ICN, CA) and incubated at 37° C. for 24-30 hours. The culture media was then aspirated; the plate was rinsed, air-dried, and fixed with 50 ul/well acetone/methanol (50:50). Viral foci were detected for enumeration by immunostaining as described previously. For antiviral testing against DV, DV serotype 2, drug incubations and titrations were performed essentially as described for WNV, except that the virus was harvested from drug-treated cultures 72 hrs after infection, and foci were stained using hybridoma culture fluid harvested from monoclonal antibody-producing hybridoma clone D1-4G2 following 3 days of incubation on Vero cells under the tragacanth overlay.

Compound toxicity assay. Compound cytotoxicity was assessed by using an MTT based toxicity assay kit (Sigma, St. Louis, Mo.) as described elsewhere. Briefly, cells cultured under conditions identical to those used in the viral assay were incubated with various concentrations of the compound for 72 hours. MTT was added to the media to a final concentration of 0.5 mg/ml and was incubated for 3 hours at 37 C. After the culture media was removed, formazan crystals was dissolved by adding 150 ul of solubilization solution (10% Triton X-100, 0.1N HCl in anhydrous isopropanol) for 15-30 minutes. The absorbance of the dissolved formazan was measured spectrophotometrically at 570 nm with absorbance at 690 nm as background.

Results

Figure 6:
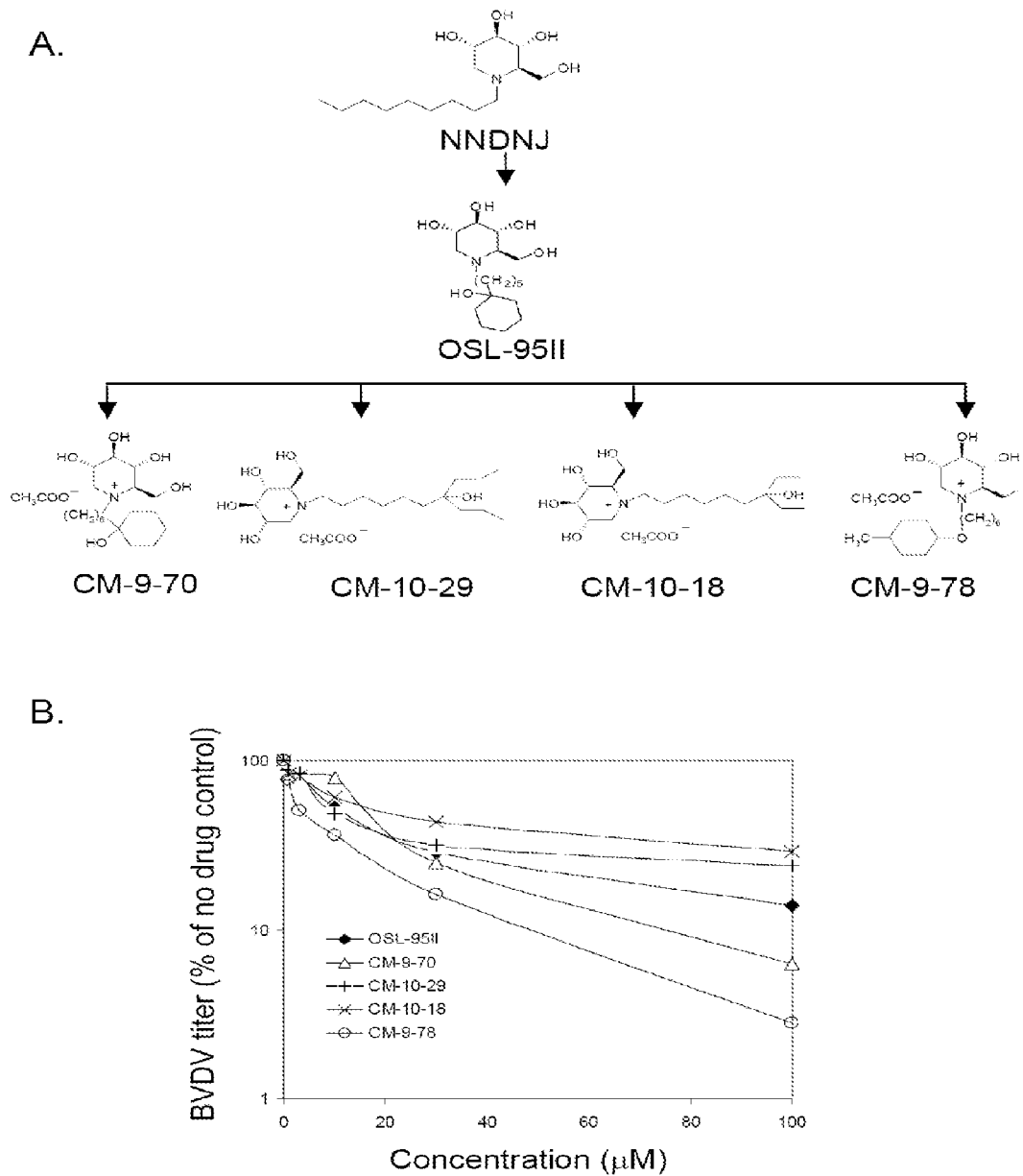

Previously, introduction of an oxygen atom into nitrogen linked alkylated side chain, would reduce cytotoxicity, but compromise antiviral efficacy. The imino sugar OSL-95II, which has a 5-carbon alkylated side chain with a terminal hydroxylated cycloalkyl structure shown in FIG. 6A, demonstrated reduced cytotoxicity but retained antiviral activity. These results suggest that terminal ring structure and/or oxygenation of nitrogen linked side chains are important for improvement of tolerance. In order to further improve efficacy and yet maintain the low toxicity, the following modifications were performed on the nitrogen linked side chain based on the structure of OSL-95II: (i) change the length of the alkylated side chain, (represented in FIG. 1A, CM-9-70); (ii) open the terminal ring structure (FIG. 6A, CM-10-18); (iii) move the oxygen atom from the terminal ring to the alkylated side chain (FIG. 6A, CM-9-78).

As shown in FIG. 6B and Table 4, while maintaining low toxicity in MDBK cells (CC50 >500 μM) which is significantly less toxic than NNDNJ, all four representative compounds demonstrated anti-BVDV activity in yield reduction assays. In particular, compared with OSL-95II, change of the length of the alkylated side chain from 5-carbon to 6-carbon (CM-9-70) retains similar antiviral activity. Furthermore, to demonstrate the requirement of terminal ring structure, the terminal ring structure was opened with or without trimming of the branch to generate CM-10-29 and CM-10-18. Both compounds maintain antiviral activity that is comparable to OSL-95II, especially for CM-10-29, which remains the 6 carbon branch structure after opening of the ring. This result suggests that in addition to ring structure, other terminal structures may also contribute to the optimization of imino sugar antiviral activity. Interestingly, for CM-9-78, which has oxygen atom located within side chain rather than as a hydroxyl group in the ring structure, the antiviral efficacy, especially the EC90 value is significantly improved compared to OSL-95II. Since hydroxyl group in the ring structure is considered to be prone to subject to hydrolysis reaction, this modification may represent the consequence of stabilization of the active component.

Change in the Composition of Terminal Ring Structure Based on CM-9-78

In order to further improve antiviral activity, CM-9-78 was modified at the terminal ring structure. The structures of these compounds are shown in FIG. 7.

Figure 7:
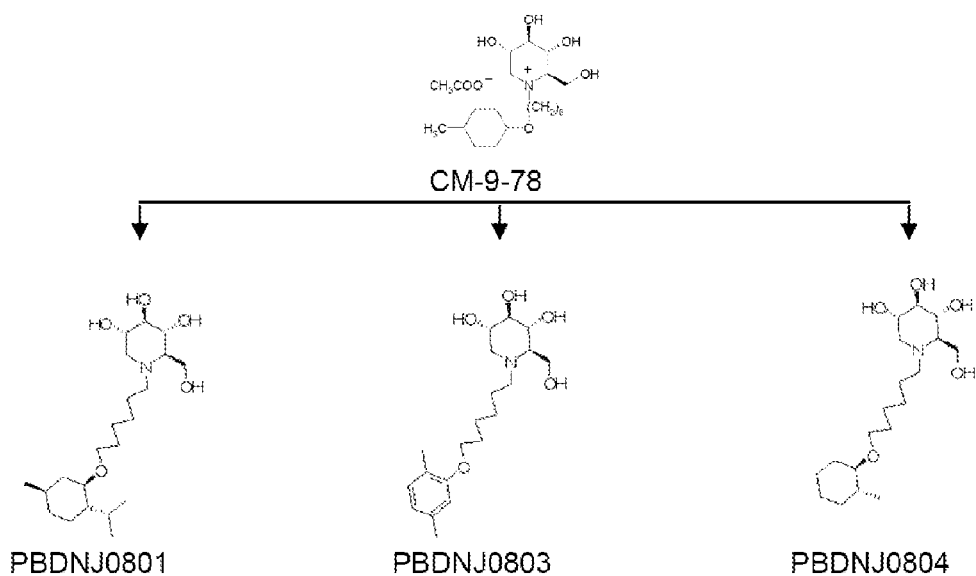
Figure 7:
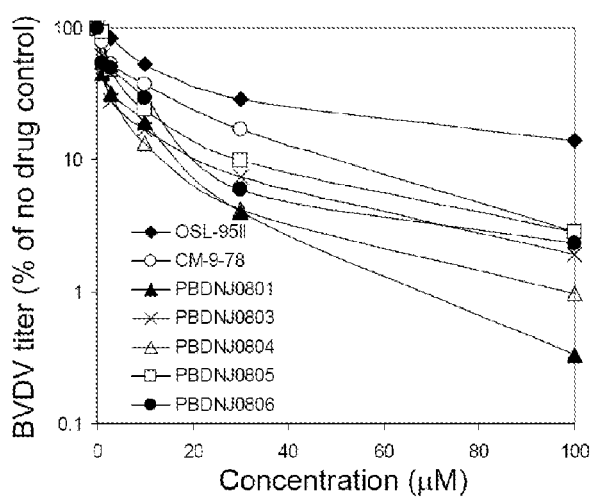

As shown in FIG. 7 and Table 4, all these compounds dramatically reduce EC50 and EC90 values in BVDV yield reduction assay. At 100 μM concentration, treatment with these compounds reduce BVDV titer at least 1 log more than that treated with OSL-95II. PBDNJ0801 showed similar CC50 as compared with NNDNJ, but with dramatically improved antiviral efficacy. The other compounds show CC50 equal or more than 500 μM and overall selection indexes (SI, the ratio of EC50 over CC50) at least 130.

TABLE 4

Summary of anti-BVDV activity and cytotoxicity of novel imino sugar derivatives in comparison with NNDNJ and OSL-95II

| | BVDV | | |
|---|---|---|---|
| | EC50 | EC90 | CC50 in MDBK cells |
| NNDNJ | 7.3 ± 0.4 | 71 ± 7.1 | 245 ± 134 |
| OSL95-II | 10.9 ± 2.7 | >100 | >500 |
| CM-9-70 | 18 ± 0 | 82.5 ± 0 | >500 |
| CM-10-18 | 22 ± 8.5 | >100 | >500 |
| CM-9-78 | 8.1 ± 3.4 | 59 ± 22 | >500 |
| PBDNJ0801 | 1.6 ± 1.2 | 14.8 ± 3.9 | 235 ± 21 |

TABLE 4-continued

Summary of anti-BVDV activity and cytotoxicity of novel imino sugar derivatives in comparison with NNDNJ and OSL-95II

| | BVDV | | |
|---|---|---|---|
| | EC50 | EC90 | CC50 in MDBK cells |
| PBDNJ0803 | 3.7 ± 3.8 | 29.2 ± 29 | 485 ± 21 |
| PBDNJ0804 | 3 ± 1.4 | 13 ± 1.7 | >500 |

TABLE 5

Summary of anti-DV, anti-WNV and cytotoxicity of novel imino sugar derivatives

| | DV | | WNV | | |
|---|---|---|---|---|---|
| | EC50 | EC90 | EC50 | EC90 | CC50 in BHK cells |
| OSL95-II | 4 | 8.7 | 4.5 | ND | >100 |
| CM-9-78 | 6.75 | 13 | ND | ND | >40 |
| PBDNJ0801 | 0.1 | 0.2 | 4.75 | 19 | 70 |
| PBDNJ0803 | 0.1 | 0.6 | 1.5 | 20 | 75 |
| PBDNJ0804 | 0.075 | 0.6 | 3.5 | 33 | 70 |

Antiviral Activity of Novel Imino Sugar Derivatives Against DV and WNV Infection The antiviral effect of CM-9-78 and its structurally related derivatives PBDNJ0801, PBDNJ0803, and PBDNJ0804 were tested against DV and WNV infection in BHK cells. BVDV infected MDBK cells have been used as a model system for screening of antiviral agent against many members of flaviviridae family. Table 5 compares OSL-95II in DV infection and WNV infection with CM-9-78 and its structurally related derivatives. So while CM-9-78 shows comparable activity with OSL-95II, PBDNJ0801, PBDNJ0803, and PBDNJ0804 show dramatically increased antiviral activity, with EC90 at submicromolar concentrations and SI of >900. In WNV infection, all these compounds show similar efficacy, which is in general, less sensitive than that of DV infection.

Although the present invention has been described with references to specific embodiments, workers skilled in the art will recognize that many variations may be made therefrom, and it is to be understood and appreciated that the disclosures in accordance with the invention show only some preferred embodiments and advantages of the invention without departing from the broader scope and spirit of the invention. It is to understood and appreciated that these discoveries in accordance with this invention are only those which are illustrated of the many additional potential applications that may be envisioned by one of ordinary skill in the art, and thus are not in any way intended to be limiting of the invention. Accordingly, other objects and advantages of the invention will be apparent to those skilled in the art from the detailed description together with the claims.

What is claimed:

1. A method of inhibiting production of enveloped viruses with a glycosylated envelope in a subject comprising administering a sufficient amount of an anti-viral composition into the subject to contact a mammalian cell infected by said enveloped virus with an effective micromolar amount of the anti-viral composition comprising a 1,5-dideoxy-1,5-imino-D-glucitol derivative selected from the group consisting of PBDNJ-0801-A, PBDNJ-0802-A, PBDNJ-0803-A, PBDNJ-0804-A, PBDNJ-0805-A, PBDNJ-0806-A, PBDNJ-0807-A, and PBDNJ-0808-A and compounds which are pharmaceutically acceptable salts thereof.

2. The method of claim 1 where the enveloped virus is a flavivirus.

3. The method of claim 2 where the flavivirus is selected from the group consisting of Dengue, West Nile, Bovine Viral Diaherra virus, Japanese Encephalitis virus, arenaviridae, filoviridae, and bunyaviridase.

4. The method of claim 3 where an additional antiviral agent is used in combination with said antiviral composition to inhibit production of said enveloped viruses.

5. The method of claim 4 where the additional antiviral agent is ribavirin.

6. A 1,5-dideoxy-1,5-imino-D-glucitol derivative compound having a formula of PBDNJ-0808-A and pharmaceutically acceptable salts thereof.

* * * * *